United States Patent [19]

Maley et al.

[11] Patent Number: 4,983,515

[45] Date of Patent: Jan. 8, 1991

[54] LABELED CRYOPRESERVED CELLS FOR USE AS TARGETS IN CYTOTOXICITY ASSAYS

[75] Inventors: Derrick T. Maley, Hadden Township, N.J.; Agneta K. Nordstrom, Rutledge, Pa.

[73] Assignee: E. I. du Pont de Nemours and Company, Wilmington, Del.

[21] Appl. No.: 311,513

[22] Filed: Feb. 16, 1989

[51] Int. Cl.$^5$ .......................... C12Q 1/02; C12N 5/00
[52] U.S. Cl. ........................................... 435/29; 435/2; 435/240.1; 435/240.2; 436/519; 436/546
[58] Field of Search .................. 436/546, 519; 435/29, 435/2, 240.1, 240.2

[56] References Cited

U.S. PATENT DOCUMENTS 4,532,203 7/1985 Ullman et al. ..................... 435/7

OTHER PUBLICATIONS

Becker et al., Biochimica et Biophysica Acta, pp. 408–417, vol. 968 (1988).
Franco et al., Life Sciences, pp. 2763–2768, vol. 32 (1983).
Shannon & Macy, *Tissue Culture Methods and Applications* (Eds. Kruse and Patterson), Academic Press, New York (1973) pp. 712–718.
Blomber et al., *J. Immunological Methods* (1986) 86:225–229.
Blomberg et al., *J. Immunological Methods* (1986) 92:117–123.
Granberg et al., *J. Immunological Methods* (1988) 114:191–195.
Henney, *J. Immunol.* (1973) 110:73–84.
Perlmann & Holm, *Advances in Immunology* (Eds. Dixon and Kunkel), Academic Press, New York (1969) 11:117–193.
Hemmiläet al., *Anal Biochem.* (1984) 137:335–343.
Brennan et al., *J. Imm. Methods* (1988) 112:121–131.

Primary Examiner—Sam Rosen

[57] ABSTRACT

Biological cells which are fluorophore-labeled can be stored frozen for a long period of time. After thawing the cells can be used as targets in fluorophore-release cytotoxicity assays.

13 Claims, No Drawings

LABELED CRYOPRESERVED CELLS FOR USE AS TARGETS IN CYTOTOXICITY ASSAYS

BACKGROUND OF THE INVENTION

The cryopreservation of cells has been in practice for many years (Shannon and Macy, in *Tissue Culture Methods and Applications* (Eds. Kruse and Patterson) Academic Press, New York (1973) pp. 712–718). The use of europium-labeled target tumor cells in an assay of natural killer cell cytotoxicity activity has been previously described by Blomberg et al. (*J. Immunological Methods* (1986) 86:225-229; *J. Immunological Methods* (1986) 92:117-123; Granberg et al. *J. Immunological Methods* (1988) 114:191-195). Cytotoxicity assays are used to test whether cells or drugs or biological agents (e.g., toxins, complement, lytic proteins, microorganisms and viruses) are toxic to target cells. For example, cytotoxicity assays are used to evaluate the activity of lymphocytes for adoptive immunotherapy of cancer (Rosenberg, U.S. Pat. No. 4,690,915 (1987)).

SUMMARY OF THE INVENTION

We have discovered that biological cells which are europium-labeled can be stored frozen for a long period of time and can be used subsequently following thawing, in cytotoxicity assays as targets for different kinds of effector cells (Henney *J. Immunol.* (1973) 110:73-84; Perlmann and Holm, in *Advances in Immunology* (Eds. Dixon and Kunkel) Academic Press, New York (1969) 11:117-193), such as cytotoxic T lymphocytes (CTLs), natural killer (NK) cells, lymphokine activated killer (LAK) cells, and tumor infiltrating lymphocytes (TIL), and for testing the cytotoxicity of drugs and biological agents such as toxins, complement, lytic proteins, microorganisms and viruses. The advantages of such europium-labeled cryopreserved cells include the fact that the label is non-radioactive and non-toxic, and is extremely sensitive. i.e., can be detected at low concentrations. Moreover, the frozen batches of labeled cells provide reproducibility of assays within and between labs and eliminate the labor and cost for the user to culture and label the target cells, as well as the storing and transport of radioactive material. In short, the advantages provided by the invention are safety, reproducibility, user friendliness, and the saving of cost and time.

It is expected that cells which are labeled with other fluorophores for example other lanthanides such as terbium (Hemmilä et al. *Anal. Biochem.* (1984) 137:335-343) and fluorescent dyes such as H33342 (Brennan et al. *J. Imm. Methods* (1988) 112:121-131) can also be frozen, thawed and used as targets in cytotoxicity assays. Our invention encompasses any cryopreserved, fluorophore-labeled, viable biological cells which after thawing are suitable for use as target cells in cytotoxicity assays.

DETAILED DESCRIPTION OF THE INVENTION

Tumor cell lines were cultured in 37° C., 5% $CO_2$ in growth medium and fed the day prior to labeling. The cells used for labeling with europium are listed in Table 1 and include tumor cell lines and freshly isolated normal and tumor cells. For initial studies described below, K562, IM9 and Raji cells were examined. At the time of labeling, the cells were first washed in a HEPES buffer (50 mM HEPES pH 7.4, 93 mM NaCl, 5 mM KCl, 2 mM MgCl) and labeled at room temperature in the same buffer containing $EuCl_3$ (20 to 400 mM), diethylene triamine penta acetate (100 μM to 2 mM)(DTPA) and dextran sulphate (500 μg/ml) for about 15 minutes. The molar ratio of $EuCl_3$/DTPA is always 1/5. The labeling was terminated by addition of $Ca^{2+}$ (4 mM final) and incubation for 5 minutes, and the cells were then washed once in the HEPES buffer supplemented with $Ca^{2+}$ (2 mM) and glucose (10 mM) and washed once in RPMI 1640, 5% FCS. The cells were then resuspended in RPMI 1640, 10% FCS, 7 to 10% DMSO, at a concentration of about $2 \times 10^6$ cells/mL, aliquoted into cryovials and stored frozen at −80° C. or in liquid nitrogen or on dry ice. After different lengths of time, vials with cells were thawed, washed in medium and the cells were tested in cytotoxicity assays, tested for survival, and for uptake and spontaneous release of DTPA-chelated europium. The europium was found to be specifically released from the labeled cells killed by the effector cells in the cytotoxicity assay. Released DTPA-chelated europium was quantitated by sampling small aliquots of cell free supernatants which were mixed with an enhancement solution (including a β-diketone, Pharmacia-LKB) and the europium fluorescence measured in a time resolved fluorometer (Arcus 1230, Pharmacia-LKB).

We determined whether the labeled cells could retain europium label through the freezing and thawing procedure without being spontaneously released. We discovered that when europium-labeled cells are frozen and thawed, the europium is retained by the cells and that the spontaneous release during subsequent assays after thawing is low.

We also determined whether the labeled and frozen cells would effectively retain the europium label during frozen storage for different lengths of time. There was no significant difference in label retention or spontaneous release whether the cells were stored for 1 day, 17 days, 8 months or 16 months. It was found that the numbers of viable cells recovered varied somewhat from sample to sample. As detailed below, however, the nonviable cells in the sample are shown not to interfere with the cytotoxicity assay.

The reproducibility of label incorporation and % spontaneous release between different vials of the same batch and between different batches of the same cell type was tested. No significant difference was found among different vials from the same batches of cells when incorporation and % spontaneous release of europium label was measured. However, there was a difference in the uptake of europium by the same cell line between batches. There was found to be no significant difference in the % spontaneous release between these different cultures.

We determined whether the europium-labeled and frozen cells could be used as targets in cytotoxicity assays following thawing. Results showed no difference between labeled frozen and labeled unfrozen cells; between frozen cells stored in liquid $N_2$ or at −80° C.; or between labeled cells frozen in a controlled freezing machine before storage in liquid $N_2$ or by manual means used to cryopreserve tissue culture cells.

Tests were made to determine the ability of labeled, fresh non-cryopreserved and cryopreserved cells to be killed by the same effector cells. There was no significant difference between fresh and cryopreserved cells to be killed by LAK cells.

Our discovery that labeled cells can be used in cytotoxicity assays following labeling of batches of cells and cryopreservation of the labeled cells provides substantial convenience and a high degree of time and cost saving to the user. It also makes it possible to use cells from the same batch in assays over a long period of time and/or in different laboratories at different times.

GROWTH AND MAINTENANCE OF MAMMALIAN CELLS USED FOR LABELING

The cell lines used in our studies, listed in Table 1, were grown in the appropriate medium as specified in the *American Type Culture Collection Catalogue of Cell Lines & Hybridomas* (Rockville, MD) in a 5% $CO_2$ incubator at 37° C.

In order to obtain reliable cell labeling and cytotoxicity assay results, the cells to be labeled and frozen should be in as healthy condition as possible, >85% alive is preferred, prior to labeling and freezing. Fresh tumor cells should be labeled before initial freezing if possible. They can be cultured or at least be conditioned in 37° C., 5% $CO_2$ before labeling and freezing.

TABLE 1
Cell Types Labeled with Europium

| Cell Lines | | Cells Frozen and Thawed |
|---|---|---|
| K562 | Human chronic myelogenous leukemia | + |
| Raji | Human Burkitt lymphoma (ATTCC CCL 86) | + |
| Daudi | Human Burkitt lymphoma (ATCC CCL 213) | + |
| IM9 | Human lymphoblast (ATCC CCL 159) | + |
| Jurkat | Human lymphoma | |
| A-498 | Human kidney carcinoma (ATCC ATB 44) | |
| SK-BR-3 | Human breast cancer (ATCC HTB 30) | + |
| U937-2 | Human histiocytic lymphoma (ATCC CRL 1593) | + |
| SKMel 37 | Human melanoma | + |
| SKMel 28 | Human melanoma (ATCC HTB 72) | + |
| M14 | Human melanoma | + |
| M20 | Human melanoma | + |
| SKMel 119 | Human melanoma | + |
| A599E1 | Colon carcinoma human | |
| HT29 | Adenocarcinoma human | |
| HM54 | Hamster melanoma | + |
| 107C3 | Guinea pig tumor cell line | |
| EL-4 | Mouse lymphoma | |
| P815 | Mouse mastocytoma | + |
| YAC-1 | Mouse lymphoma | + |
| B16 | Mouse melanoma | |
| F-10 | Mouse melanoma | |
| LSTRA | Mouse T cell leukemia | |
| L5178y | Mouse lymphoma | |
| MC105 | Mouse sarcoma | |
| MC38 | Mouse sarcoma | |
| B16W | Mouse melanoma | + |
| J-32 | | |
| HR-1 | Mouse thymoma, NK sensitive | |
| L929 | Mouse fibroblast | |
| Fresh Normal Cells | | |
| HS27 | Newborn human foreskin (prim) | |
| PBL | Human peripheral blood lymphocytes | + |
| Oocyte | Frog oocyte | |
| Fresh Human Tumor Cells | | |
| | Lymphoma | |
| | Leukemia | |
| | Melanoma | |
| | Ovarian | |
| | Thyroid | |
| | Pancreatic | |
| | Colon | |
| | Renal Carcinoma | |
| | Sarcoma | |

TABLE 1-continued
Cell Types Labeled with Europium

| | | |
|---|---|---|
| | Andrews TIL-Tumor (from Glasgow) | |

EUROPIUM LABELING OF CELLS

All cell lines were washed and fed with new medium the day prior to labeling. $5 \times 10^6$ to $1 \times 10^7$/mL tumor cells in polypropylene tubes (Sarstedt, Inc., Princeton. NJ) were washed once in a buffer, designated BI, containing 50 mM HEPES, 93 mM NaCl, 5 mM KCl and 2 mM $MgCl_2$, pH 7.4. The Z cells were labeled in BI supplemented with 20 $\mu$M of $EuCl_3$ (Fuka, Ronkonkoma, NY) and 100 $\mu$M of diethylene triamine penta acetate (DTPA) (Sigma, St. Louis), and to which 500 $\mu$g/ml of dextran sulphate (Pharmacia Fine Chemicals, Piscataway, NJ) was added just prior to mixing with the cells. Five times higher concentration of $EuCl_3$ and DTPA was used for labeling Raji cells than was used for labeling K562 cells, since the Raji cells are smaller and more difficult to label than K562 cells. A concentration of $EuCl_3$ of 100 to 400 $\mu$M and a corresponding concentration of DTPA 500 $\mu$M to 2 mM has been used successfully. The molar ratio of $EuCl_3$/DTPA is always 1/5. Labeling was performed at room temperature for 15 minutes with gentle mixing with pasteur pipette every 3 minutes.

The labeling was terminated by adding $CaCl_2$ to a final concentration of 4 mM followed by another 5 minutes of incubation. The cells were then washed once with BI supplemented with 2 mM $CaCl_2$ and 10 mM glucose. The labeled cells may then be washed 2-times in this buffer and then washed 2-times in RPMI 1640, 5% FCS. The labeled and washed tumor cells were resuspended in RPMI 1640, 10% FCS, 8% DMSO and counted, and the concentration adjusted to $2 \times 10^6$/mL live cells.

Other labels and labeling procedures may also be used for labeling target cells, such as the Hoechst dye no. 33342 fluorescent label (Brenan and Parish (1988) *J. Immunol. Methods* 112:121–131) and other lanthanides such as terbium (Hemmilä *et al. Anal. Biochem.* (1984) 137:335–343).

FREEZING AND THAWING OF CELLS

Following labeling, the cells to be frozen are resuspended in growth medium containing 10% DMSO and dispensed into cryovials (Corning Glassworks, Corning, NY or A/S NUNC, Roskilde, Denmark or Sarstedt) at $10^6$ to $10^7$ cells per 1 mL per vial and slowly frozen in a controlled temperature freezing machine to $-70°$ C. in 50 min, thereafter stored in liquid nitrogen or a $-80°$ C. freezer or covered with dry ice in a styrofoam box. The DMSO used in the freezing medium must be of tissue culture grade. Inclusion of 5% to 10% DMSO. or some other cryoprotectant such as glycerol, in the freezing medium is essential to maintain cell viability. Test samples were also frozen at $-20°$ C. for 1 hour and thereafter moved to $-80°$ C. or at 4° C. for 1 hr followed by $-80°$ C. No significant differences were found in the characteristics (cell viability, label spontaneous release) of the cells following freezing using the different freezing procedures as long as the temperature is reduced slowly.

Cell concentration is not critical; however, a concentration of $10^6$ to $10^7$ cells/vial is usually used. The appropriate number of cells stored per vial would probably be determined by the recovery expected and the number of assays that could be run.

Thawing and Washing: The frozen cells are quickly thawed by immersing the frozen vials into a 37° C. water bath. Thawing should occur as quickly as possible. Agitation of the vials facilitates this. The cell suspension is placed into a polypropylene centrifuge tube and diluted with 10 ml of the appropriate growth medium containing 10% FCS. The cells are pelleted using 1000 RPM for 10 min. The supernatant is discarded. The cells are then washed 2×with the same medium containing 5% FCS. The washing steps remove the DMSO and any europium that was released from cells that did not survive the freezing process. The concentration of trypan blue-excluding cells is determined by hemocytometer counting and the cells resuspended in assay medium at the appropriate concentration. The trypan blue exclusion assay is a standard assay of cell viability.. dead cells do not exclude trypan blue and are stained.

As a quality control, all batches of labeled cells are tested after freezing and thawing for survival, incorporation of marker, maximum and spontaneous release, and ability to be killed in a cytotoxicity assay.

EUROPIUM RELEASE CYTOTOXICITY ASSAY

LAK effector cells are generated from ficol-hypaque separated peripheral blood mononuclear cells cultured for 3 to 5 days in the presence of 2–10 U/mL IL-2. Cytotoxic T-lymphocytes are prepared from mixed lymphocyte tumor cultures (MLTC) where peripheral blood mononuclear cells are co-cultured with irradiated (3000 Rad) IM9 cells at a ratio of 10:1 lymphocytes:tumors, or 40:1 lymphocytes:tumors for 3 days. The resultant activated cytotoxic T-lymphocytes are grown in vitro in the presence of 2–10 U/mL IL-2 for 6 to 10 days.

Effector (killer) cells were mixed with labeled target (tumor) cells and incubated for 1 to 3 hours. The label released into the supernatant from the killed target cells was then collected after pelleting the cells. Effector cells (LAK, NK, CTL) were washed 2-times with RPMI 1640, 5% FCS, then brought to a concentration of $3 \times 10^6$ cells/mL to accommodate a highest effector/target ratio of 60:1. Serial dilutions were made with a dilution factor of 3. Four different effector:target ratios were used, always in triplicate. Assays were performed in V-shaped or U-shaped 96-well plates (Linbro, Flow Laboratories, McLean, VA) with 50 μL of effector cell suspension and 50 μL of target cell suspension per well. The cell numbers can be adjusted to accommodate different target:effector ratios.

The plates were centrifuged at 30xg for 1 minute before incubating at 37° C., 5% $CO_2$, for 1 to 3 hours. The plates were then centrifuged at 200xg for 3 minutes to pellet the cells and 20 μl of supernatant collected per well into flat bottom strips (Titertek, Flow Laboratories, Inc., McLean, VA). To eliminate any background counts from excessive europium-DTPA that had not been completely washed off the cells after labeling, 12 samples of 50 μL of target cell suspension and an equal volume of medium were centrifuged without previous incubation and 20 μl of supernatant collected. These control samples were later used as blanks when europium was measured.

DETECTION AND QUANTITATION OF EUROPIUM RELEASED

Europium was detected in a time resolved fluorometer, 1230 Arcus ® (LKB, Inc.. Gaithersburg, MD). The supernatants were collected into flat bottom strips (Titertek ®, Flow Laboratories, Inc., McLean, VA), 200 μl of enhancing solution (Delfia enhancement solution, LKB Inc., Gaithersburg, MD) was added per well, and the mixtures were gently shaken for 3 minutes before counting. Using europium, the sensitivity is up to about 100-fold greater than that obtained using $^{51}Cr$ as the label. This greater sensitivity using europium allows much fewer cells to be used in the cytotoxicity assay than when $^{51}Cr$ is used as the label. The % specific marker release was determined by the following formula:

$$\frac{\text{Sample Counts} - \text{Spontaneous Release Counts}}{\text{Maximum Release Counts} - \text{Spontaneous Release Counts}}$$

CHARACTERISTICS OF EUROPIUM-LABELED CELLS FOLLOWING CRYOPRESERVATION

Studies were carried out to determine whether the europium-labeled target cells could be stored frozen and be useful as target cells in cytotoxicity assays after thawing. Target cells were labeled and then frozen, using the manual freezing method. The cells were stored in liquid nitrogen, dry ice, and at −80° C. in a freezer. The cells were thawed, retained europium was counted, and the cell viability determined.

Table 2 shows the viabilities of labeled K562 cells, and Raji cells over a period of two weeks, from two experiments. Similar results were obtained using IM9 cells.

TABLE 2

K562, Raji, or IM9 cells, labeled with Europium were frozen and stored under different freezer conditions. Liquid nitrogen (N2), −80° C., or dry ice (CO2). The cells were thawed on various days. and the % viable cells determined using trypan-blue exclusion by live cells counted on a hemocytometer.

| 1st Experiment, Recovery of Cells After Thawing | | | | | | |
|---|---|---|---|---|---|---|
| | K562 % Viable | | | Raji % Viable | | |
| Day | N2 | −80 | Dry Ice | N2 | −80 | Dry Ice |
| 1 | 60 | 60 | 60 | 60 | 60 | 60 |
| 2 | 66 | 73 | 67 | 68 | 68 | 57 |
| 3 | 77 | 59 | 70 | 69 | 56 | 52 |
| 4 | 69 | 61 | 63 | 61 | 61 | 60 |
| 7 | 68 | 71 | 68 | 71 | 52 | 66 |
| 17 | 73 | 69 | 61 | 69 | 67 | 49 |

| 2nd Experiment, Recovery of Cells After Thawing | | | | | | |
|---|---|---|---|---|---|---|
| | K562 % Viable | | | Raji % Viable | | |
| Day | N2 | −80 | Dry Ice | N2 | −80 | Dry Ice |
| 1 | 77 | 77 | 77 | 60 | 60 | 60 |
| 4 | 84 | 77 | 81 | 63 | 54 | 50 |
| 5 | 72 | 71 | 76 | 46 | 52 | 38 |
| 6 | 68 | 74 | 68 | 53 | 58 | 49 |
| 7 | 73 | 72 | 74 | 66 | 51 | 38 |
| 14 | 79 | 67 | 61 | 56 | 53 | 33 |

| | IM9 % Viable | | |
|---|---|---|---|
| Day | N2 | −80 | Dry Ice |
| 1 | 81 | 81 | 81 |
| 4 | 83 | 80 | 76 |
| 5 | 66 | 72 | 70 |
| 6 | 74 | 69 | 61 |
| 7 | 71 | 75 | 65 |

TABLE 2-continued

K562, Raji, or IM9 cells, labeled with
Europium were frozen and stored under different
freezer conditions. Liquid nitrogen (N2), −80° C.,
or dry ice (CO2). The cells were thawed on various
days. and the % viable cells determined using
trypan-blue exclusion by live cells counted on a
hemocytometer.

| 14 | 83 | 73 | 66 |

The number of viable cells recovered was variable. Because of this, there will be varying numbers of dead cells in each assay. These dead cells could create problems by retaining their europium which would drive up the apparent total counts. This would effectively reduce the % europium released. On the other hand, the dead cells might continue to leak europium, which would drive up the spontaneous release. This might create unacceptable noise levels in the assay. Another problem could arise if the dead cells competed with the live targets. This would also drive down the apparent killing. Experiments were performed that showed that the label is washed away from dead cells and the dead cells do not interfere in the assays.

Cells frozen using a 1% DMSO concentration in the freezing medium produces cell cultures with less than 10% living cells after thawing. These dead cells can be added back to assays to see their effects, or compared to cultures that contain 90% live targets.

Table 3 shows the results of experiments to determine whether dead target cells hold onto their label or whether they continue to leak europium after washing. Labeled targets were frozen in 5% DMSO or 1% DMSO, then thawed. The thawed cells were resuspended in 10 ml of medium. The cell suspensions were sampled and counted. This represents the total releasable counts from the first wash. The cells were then centrifuged. The resultant supernatant was also sampled, then removed. These counts represented the spontaneous release from the first wash. This cycle of cell suspensions and supernatants was continued six more times. Table 3 (left) shows that there is a constant low level release from the live cells, but the label is completely washed from the dead cells. Table 3 (right) shows that the live cells continue to hold their label, while the dead cells do not hold europium. Therefore, only live cells retain the europium label within the cell after washing.

TABLE 3

Europium-labeled K562 cells were frozen
using different concentrations of DMSO. Cells do
not survive 1% DMSO, but will survive 5% DMSO. The
% europium remaining in the supernatant (left) and
cell suspension (right) was quantitated for each
successive wash.

| | Supernatant % Eu Remaining | | | Cell Suspension % Eu Remaining | |
|---|---|---|---|---|---|
| | 5% DMSO | 1% DMSO | | 5% DMSO | 1% DMSO |
| Wash 1 | 100% | 100% | Wash 1 | 100% | 100% |
| Wash 2 | 2% | 1% | Wash 2 | 52% | 1% |
| Wash 3 | 1% | 0% | Wash 3 | 51% | 1% |
| Wash 4 | 1% | 0% | Wash 4 | 50% | 1% |
| Wash 5 | 1% | 0% | Wash 5 | 48% | 0% |
| Wash 6 | 1% | 0% | Wash 6 | 46% | 0% |
| Wash 7 | 1% | 0% | Wash 7 | 46% | 0% |
| Media | 0% | 0% | | | |

Experiments were performed to determine whether dead target cells compete in the cytotoxicity assay. Unlabeled dead or live IM9 cells were added to an assay containing a constant ratio of effector cells to labeled IM9 cells. Dead cells were prepared by freezing the cells in medium containing only 1% DMSO. The effectors were killer cells at a concentration of $10^6$/mL. The labeled targets were added at a concentration of $10^5$/mL. Increasing numbers of unlabeled IM9 cells were added. Only the live IM9 cells were shown to compete in this cytotoxicity assay. The ability of MLTC-derived cytotoxic lymphocytes to kill europium-labeled K562 cells was tested at 3 different effector:-target cell ratios, with increasing concentrations of added dead K562 cells. Again, the dead target cells were shown not to compete in the cytotoxicity assay even in the presence of a 7-fold excess of dead europium-labeled K562 cells.

Experiments were performed to show the reproducibility of the killing assay using multiple vials of targets from the same batch. Table 4 shows an experiment where K562 cells were labeled with europium and multiple vials of europium-labeled cells were frozen at −80° C. Three vials stored for 8 months at −80° C. were thawed, washed, counted, and set up to the same concentration of live cells. When these individual targets were tested against two effector cultures, one that had high levels of killing, and one with low levels of killing, the killing curves were identical for the three vials.

TABLE 4

Three vials of europium-labeled, frozen target
cells from the same labeling were thawed after 8
months. The target cells from each vial were washed
and counted separately so that the different vials
could be compared. They were used in cytotoxicity
assays against highly cytotoxic MLTC-derived
lymphocytes, or a culture of PHA blasts that have low
killing potential. The assay was for two hours.

| Effector | E:T | Europium-K562 Vial | | |
|---|---|---|---|---|
| | | 1 | 2 | 3 |
| MLTC | 40:1 | 99% | 101% | 99% |
| | 20:1 | 87% | 94% | 91% |
| | 10:1 | 73% | 76% | 72% |
| | 5:1 | 47% | 57% | 52% |
| PHA Blast | 40:1 | 22% | 22% | 21% |
| | 20:1 | 11% | 15% | 13% |
| | 10:1 | 2% | 7% | 6% |
| | 5:1 | −1% | 2% | 1% |

Table 5 shows similar cytotoxicity data using a variety of cryopreserved europium labeled target cells.

TABLE 5

Europium release from prelabeled, frozen and
thawed targets by different effector cultures. PBL
from three individuals were cultured for 6 days at
$2 \times 10^6$/mL in AIM V media. Control cultures were not
stimulated. MLTC cultures were stimulated with
irradiated IM9 cells at a stimulator:responder ratio
of 1:40. Mixed melanoma cultures were stimulated with
a mixture of 4 irradiated melanoma cell lines (SKMel
28, HM54, M14, and M20) each 1:40. LAK cell cultures
had 10 U/mL. IL-2 added to activate LAK cell killing.
The europium-release assay was set up using $6 \times 10^4$/mL
targets, 50 μl/well, and $2.4 \times 10^6$/mL effectors, 50
μl/well in a 96 well plate, for 2 hours.

| Donor # | 1 | 2 | 3 |
|---|---|---|---|
| Culture | % Rel. | % Rel. | % Rel. |
| Europium-K562 | | | |
| Control | 21% | 3% | 5% |
| MLTC | 47% | 53% | 62% |
| Mixed Melanoma | 15% | 14% | 29% |
| LAK | 56% | 66% | 84% |

TABLE 5-continued

Europium release from prelabeled, frozen and thawed targets by different effector cultures. PBL from three individuals were cultured for 6 days at $2 \times 10^6$/mL in AIM V media. Control cultures were not stimulated. MLTC cultures were stimulated with irradiated IM9 cells at a stimulator:responder ratio of 1:40. Mixed melanoma cultures were stimulated with a mixture of 4 irradiated melanoma cell lines (SKMel 28, HM54, M14, and M20) each 1:40. LAK cell cultures had 10 U/mL. IL-2 added to activate LAK cell killing. The europium-release assay was set up using $6 \times 10^4$/mL targets, 50 μl/well, and $2.4 \times 10^6$/mL effectors, 50 μl/well in a 96 well plate, for 2 hours.

| Donor # Culture | 1 % Rel. | 2 % Rel. | 3 % Rel. |
|---|---|---|---|
| Europium-IM9 | | | |
| Control | −4% | −1% | −4% |
| MLTC | 10% | 30% | 16% |
| Mixed Melanoma | −3% | −5% | −7% |
| LAK | 5% | 13% | 26% |
| Europium-SKMel 37 | | | |
| Control | −1% | 0% | 0% |
| MLTC | 26% | 26% | 40% |
| Mixed Melanoma | 2% | 0% | 6% |
| LAK | 35% | 47% | 73% |
| Europium-SKMel 119 | | | |
| Control | 0% | −1% | −1% |
| MLTC | 21% | 23% | 30% |
| Mixed Melanoma | −2% | 1% | 3% |
| LAK | 33% | 38% | 58% |
| Europium-SKMel 28 | | | |
| Control | −1% | 0% | −1% |
| MLTC | 5% | 14% | 9% |
| Mixed Melanoma | −2% | −1% | −1% |
| LAK | 8% | 14% | 40% |
| Europium-HM54 | | | |
| Control | 2% | 0% | 1% |
| MLTC | 20% | 29% | 45% |
| Mixed Melanoma | 2% | 1% | 9% |
| LAK | 39% | 43% | 70% |
| Europium-M14 | | | |
| Control | 3% | 0% | 3% |
| MLTC | 15% | 16% | 22% |
| Mixed Melanoma | 1% | 1% | 3% |
| LAK | 22% | 22% | 52% |
| Europium-M20 | | | |
| Control | 0% | −1% | 0% |
| MLTC | 16% | 29% | 28% |
| Mixed Melanoma | 0% | 1% | 4% |
| LAK | 23% | 35% | 65% |

Fluorophore-labeled cryopreserved cells may be used as targets in various types of cytotoxicity assays other than those specifically exemplified above. For example, the cells may be used as targets in assays to determine cytotoxicity of drugs and biological agents such as toxins, complement, lytic proteins, microorganisms and viruses. The cells may be used in tissue typing tests in which the cells (usually normal lymphocytes) are exposed to various antisera or monoclonal antibodies; antibody-dependent complement-mediated cytoxicity assays may be carried out using cryopreserved fluorophore-labeled target cells, for the purpose of determining whether there are molecular markers present on the cell which are recognized by the antibody (Lyerly et al. Proc. Natl. Acad. Sci. (1987) 84:4601–4605). Cryopreserved fluorophore-labeled target cells may also be coated with an exogenous antigen such as a viral or tumor antigen and used in cell-mediated cytotoxicity assays to detect viral or tumor antigen-specific cytotoxic effector lymphocytes. For example, CD4-positive cells may be coated with HIV-1 envelope gp120 protein and used in cytolytic assays to monitor gp120-specific cytotoxic lymphocyte levels in AIDS patients (Lyerly et al., supra). Other applications and variations of the invention will be obvious to those skilled in the art of cytotoxicity assays.

We claim:

1. Cryopreserved, fluorophore-labeled, viable biological cells which after thawing are suitable for use as target cells in cytotoxicity assays.

2. Cryopreserved, europium-labeled, viable biological cells which after thawing are suitable for use as target cells in cytotoxicity assays.

3. Cells of claim 2 which are cells of a stable mammalian cell line.

4. Cells of claim 3 which are malignant cells.

5. Cells of claim 2 which are fresh tumor cells.

6. Cells of claim 2 which are non-malignant cells.

7. Cells of claim 6 which are coated with an exogenous antigen.

8. Cells of claim 2 wherein the europium is present in the cells as a chelate of europium and a chelating agent.

9. A method of producing the cells of claim 1 which comprises (a) labeling viable biological cells with a fluorophore, (b) washing the labeled cells with buffer, (c) suspending the cells in growth medium containing a cryoprotectant, and (d) freezing the cell suspension over a period of about one hour.

10. A method of producing the cells of claim 2 which comprises (a) treating viable biological cells with a buffered solution of a soluble compound of europium and a chelating agent to label the cells with europium, (b) washing the labeled cells with buffer, (c) suspending the cells in growth medium containing a cryoprotectant, and (d) freezing the cell suspension over a period of about one hour.

11. In a fluorophore-release assay for measuring cytotoxicity of a cytotoxic agent, wherein the agent is incubated with a suspension of fluorophore-labeled target cells and the release of fluorophore from the target cells is determined by fluorescence measurement, the improvement which comprises thawing the cells of claim 1 and using the thawed cells as the target cells.

12. In a europium-release assay for measuring cytotoxicity of a cytotoxic agent selected from effector cells, drugs and biological agents, wherein the agent is incubated with a suspension of europium-labeled target cells and the release of europium from the target cells is measured by time-resolved fluorescence, the improvement which comprises thawing the cells of claim 2 and using the thawed cells as the target cells.

13. In a europium-release assay for measuring cytotoxicity of effector cells selected from natural killer cells, lymphokine-activated killer cells, cytotoxic T-lymphocytes and tumor-infiltrating lymphocytes, wherein a suspension of effector cells is incubated with a suspension of europium-labeled target cells and the release of europium from the target cells is measured by time-resolved fluorescence, the improvement which comprises thawing the cells of claim 2 and using the thawed cells as the target cells.

* * * * *